US012600956B2

(12) United States Patent
Schmitt et al.

(10) Patent No.: US 12,600,956 B2
(45) Date of Patent: Apr. 14, 2026

(54) PARAMYXOVIRUS VIRUS-LIKE PARTICLES AS PROTEIN DELIVERY VEHICLES

(71) Applicant: The Penn State Research Foundation, University Park, PA (US)

(72) Inventors: Anthony Paul Schmitt, State College, PA (US); Phuong Tieu Schmitt, State College, PA (US); Greeshma Vivekananda Ray, Cleveland, OH (US)

(73) Assignee: The Penn State Research Foundation, University Park, PA (US)

( * ) Notice: Subject to any disclaimer, the term of this patent is extended or adjusted under 35 U.S.C. 154(b) by 1167 days.

(21) Appl. No.: 17/542,337

(22) Filed: Dec. 3, 2021

(65) Prior Publication Data

US 2022/0162567 A1 May 26, 2022

Related U.S. Application Data

(63) Continuation-in-part of application No. 16/433,412, filed on Jun. 6, 2019, now Pat. No. 11,339,375, which is a continuation of application No. 15/383,324, filed on Dec. 19, 2016, now Pat. No. 10,316,295.

(60) Provisional application No. 63/146,430, filed on Feb. 5, 2021, provisional application No. 62/268,921, filed on Dec. 17, 2015.

(51) Int. Cl.
*C12N 7/00* (2006.01)
*C07K 14/005* (2006.01)
*C07K 14/81* (2006.01)
*C07K 16/10* (2006.01)
*C12N 9/02* (2006.01)

(52) U.S. Cl.
CPC .............. *C12N 7/00* (2013.01); *C07K 14/005* (2013.01); *C07K 14/8121* (2013.01); *C07K 16/1027* (2013.01); *C12N 9/0069* (2013.01); *C12N 9/0089* (2013.01); *C12Y 113/12005* (2013.01); *C12Y 115/01001* (2013.01); *C12N 2760/18022* (2013.01); *C12N 2760/18023* (2013.01); *C12N 2760/18034* (2013.01); *C12N 2760/18222* (2013.01); *C12N 2760/18223* (2013.01); *C12N 2760/18234* (2013.01); *C12N 2760/18252* (2013.01); *C12N 2760/18722* (2013.01); *C12N 2760/18723* (2013.01); *C12N 2760/18734* (2013.01)

(58) Field of Classification Search
None
See application file for complete search history.

(56) References Cited

U.S. PATENT DOCUMENTS

| | | | |
|---|---|---|---|
| 8,765,666 B2 | 7/2014 | Szolajska et al. | |
| 10,316,295 B2 | 6/2019 | Schmitt et al. | |
| 11,339,375 B2 | 5/2022 | Schmitt et al. | |
| 2006/0216702 A1 | 9/2006 | Compans et al. | |
| 2010/0120092 A1 | 5/2010 | Grgacic et al. | |
| 2011/0097355 A1 | 4/2011 | Morrison | |
| 2011/0189159 A1* | 8/2011 | Chatterjee | C07K 14/00 424/94.63 |
| 2011/0250675 A1 | 10/2011 | Bennett | |
| 2012/0087940 A1 | 4/2012 | Inoue et al. | |
| 2013/0017210 A1 | 1/2013 | Peabody et al. | |

FOREIGN PATENT DOCUMENTS

| | | |
|---|---|---|
| WO | 00/09157 | 2/2000 |
| WO | 2007/019247 A2 | 2/2007 |
| WO | 2008061243 A1 | 5/2008 |

OTHER PUBLICATIONS

Capul, et al., A cell-based luciferase assay amenable to high-throughput screening of inhibitors of arenavirus budding, Virology, Oct. 16, 2008, vol. 382, No. 1, pp. 107-114.

Coronel, E. C. et al., Nucleocapsid Incorporation into Parainfluenza Virus Is Regulated by Specific Interaction with Matrix Protein, Journal of Virology, Feb. 2001, vol. 75, No. 3, pp. 1117-1123.

Harrison, et al., Paramyxovirus assembly and budding: Building particles that transmit infections, The International Journal of Biochemistry and Cell Biology, Apr. 14, 2010, vol. 42, pp. 1416-1429.

Iwasaki, et al., The Matrix Protein of Measles Virus Regulates Viral RNA Synthesis and Assembly by Interacting with the Nucleocapsid Protein, Journal of Virology, Aug. 5, 2009, vol. 83, No. 20, pp. 10374-10383.

Kaczmarczyk, et al., Protein delivery using engineered virus-like particles, Proc. of the Natl. Acad. of Sci. U.S.A., Oct. 11, 2011, vol. 108, No. 41, pp. 16998-17003.

Li, et al., Mumps Virus Matrix, Fusion, and Nucleocapsid Proteins Cooperate for Efficient Production of Virus-Like Particles, Journal of Virology, May 13, 2009, vol. 83, No. 14, pp. 7261-7272.

Pantua et al., Requirements for the Assembly and Release of Newcastle Disease Virus-Like Particles, J. Virol. 2006, vol. 80(22), p. 11062-73.

Patch, et al., Quantitative analysis of Nipah virus proteins released as virus-like particles reveals central role for the matrix protein, Virology Journal, Jan. 4, 2007, vol. 4, No. 1, 14 pages.

Schmitt, et al., Requirements for Budding of Paramyxovirus Simian Virus 5 Virus-Like Particles, Journal of Virology, Apr. 2002, vol. 76, No. 8, pp. 3952-3964.

(Continued)

*Primary Examiner* — Benjamin P Blumel
(74) *Attorney, Agent, or Firm* — Hodgson Russ LLP

(57) ABSTRACT

Provided are compositions and methods for introducing proteins into cells. The compositions and methods relate to introducing a foreign protein as an engineered component of a paramyxovirus virus like particle (VLP). The compositions and methods pertain to modified VLPs that contain a contiguous recombinant polypeptide comprising i) all or a segment of a C-terminal domain of a paramyxovirus nucleocapsid protein and ii) a polypeptide sequence of a distinct protein that is an enzyme such as a recombinase.

8 Claims, 15 Drawing Sheets

Specification includes a Sequence Listing.

(56)     References Cited

OTHER PUBLICATIONS

Schmitt, et al., The C-Terminal End of Parainfluenza Virus 5 NP Protein is Important for Virus-Like Particle Production and M-NP Protein Interaction, Journal of Virology, Oct. 13, 2010, vol. 84, No. 24, pp. 12810-12823.

Tan, et al, Solubility, immunogenicity and physical properties of the nucleocapsid protein of Nipah virus produced in *Escherichia coli*, Journal of Medical Virology, Mar. 18, 2004, vol. 73, Issue 1, pp. 105-112.

Tscherne, et al., An Enzymatic Virus-Like Particle Assay for Sensitive Detection of Virus Entry, Virol Methods, Feb. 2010, vol. 163, No. 2, pp. 336-343.

Wolf, et al., A catalytically and genetically optimized beta-lactamase-matrix based assay for sensitive, specific, and higher throughput analysis of native henipavirus entry characteristics, Virology Journal, Jul. 31, 2009, vol. 6, No. 119, 11 pages.

Ray, et al., C-Terminal DxD-Containing Sequences within Paramyxovirus Nucleocapsid Proteins Determine Matrix Proten Compatibility and Can Direct Foreign Proteins into Budding Particles, Journal of Virology, Jan. 20, 2016, pp. 3650-3660.

* cited by examiner

H

A

B

PARAMYXOVIRUS VIRUS-LIKE PARTICLES AS PROTEIN DELIVERY VEHICLES

CROSS REFERENCE TO RELATED APPLICATIONS

This application claims priority to U.S. Provisional Application No. 63/146,430, filed Feb. 5, 2021, the entire disclosure of which is incorporated herein by reference. This application is also a continuation-in-part of U.S. application Ser. No. 16/433,412, filed Jun. 6, 2019, which is a continuation of U.S. application Ser. No. 15/383,324, filed Dec. 19, 2016, now U.S. Pat. No. 10,316,295, which claims priority to U.S. Provisional Application No. 62/268,921, filed Dec. 17, 2015, the entire disclosures of each of which are incorporated herein by reference.

STATEMENT REGARDING FEDERALLY SPONSORED RESEARCH OR DEVELOPMENT

This invention was made with government support under Grant Nos. AI070925 and AI121880 awarded by the National Institutes of Health and under Hatch Act Project Nos. PEN04215 and PEN04497 awarded by the United States Department of Agriculture/NIFA. The Government has certain rights in the invention.

SEQUENCE LISTING STATEMENT

The instant application contains a Sequence Listing which has been submitted electronically in ASCII format and is hereby incorporated by reference in its entirety. Said ASCII copy was created on Dec. 3, 2021, is titled "PSU_2015_4396.txt", and is 3,597 bytes in size.

BACKGROUND OF THE DISCLOSURE

There is an ongoing and unmet need for compositions and methods that are useful for protein delivery to a variety of cell types for a variety of purposes. The present disclosure pertains to this need.

SUMMARY

The present disclosure provides compositions and methods for introducing proteins into cells. The compositions and methods relate to introducing a foreign protein as an engineered component of a paramyxovirus virus like particle (VLP). The compositions and methods pertain to modified VLPs that contain a contiguous recombinant polypeptide comprising i) all or a segment of a C-terminal domain of a paramyxovirus nucleocapsid protein and ii) a polypeptide sequence of a distinct protein that is an enzyme, which may be any recombinase, including but not limited to Cre recombinase.

US 12,600,956 B2

3 washing (8 washes) with PBS in all cases except in panel G, where minimal washing (a single PBS wash) was employed where indicated. Cells were visualized using a fluorescence microscope. Error bars indicate standard deviations (n=3). *P<0.05, P<0.01, *P<0.001, Welch's t-test.

Figure 5:
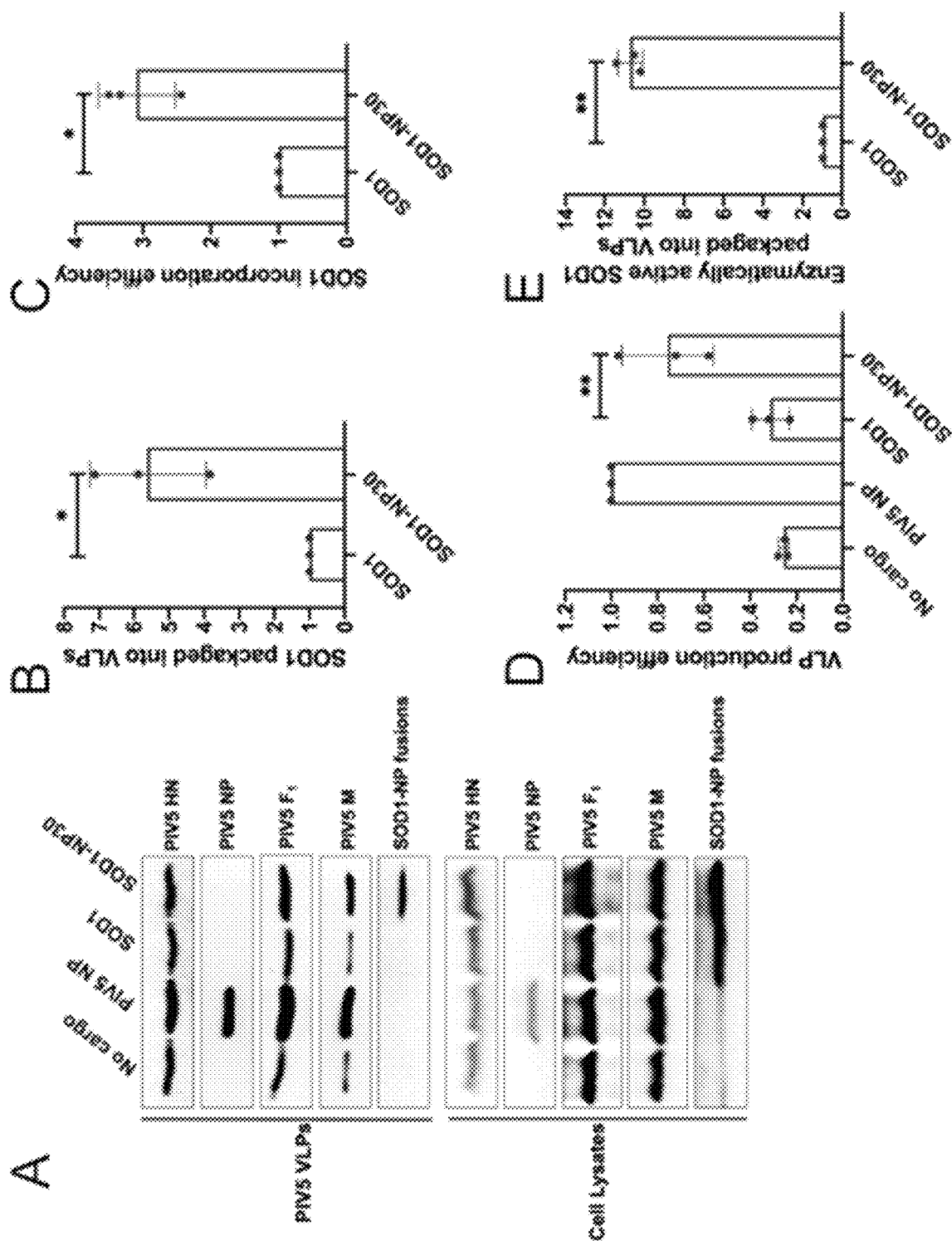
Figure 5:
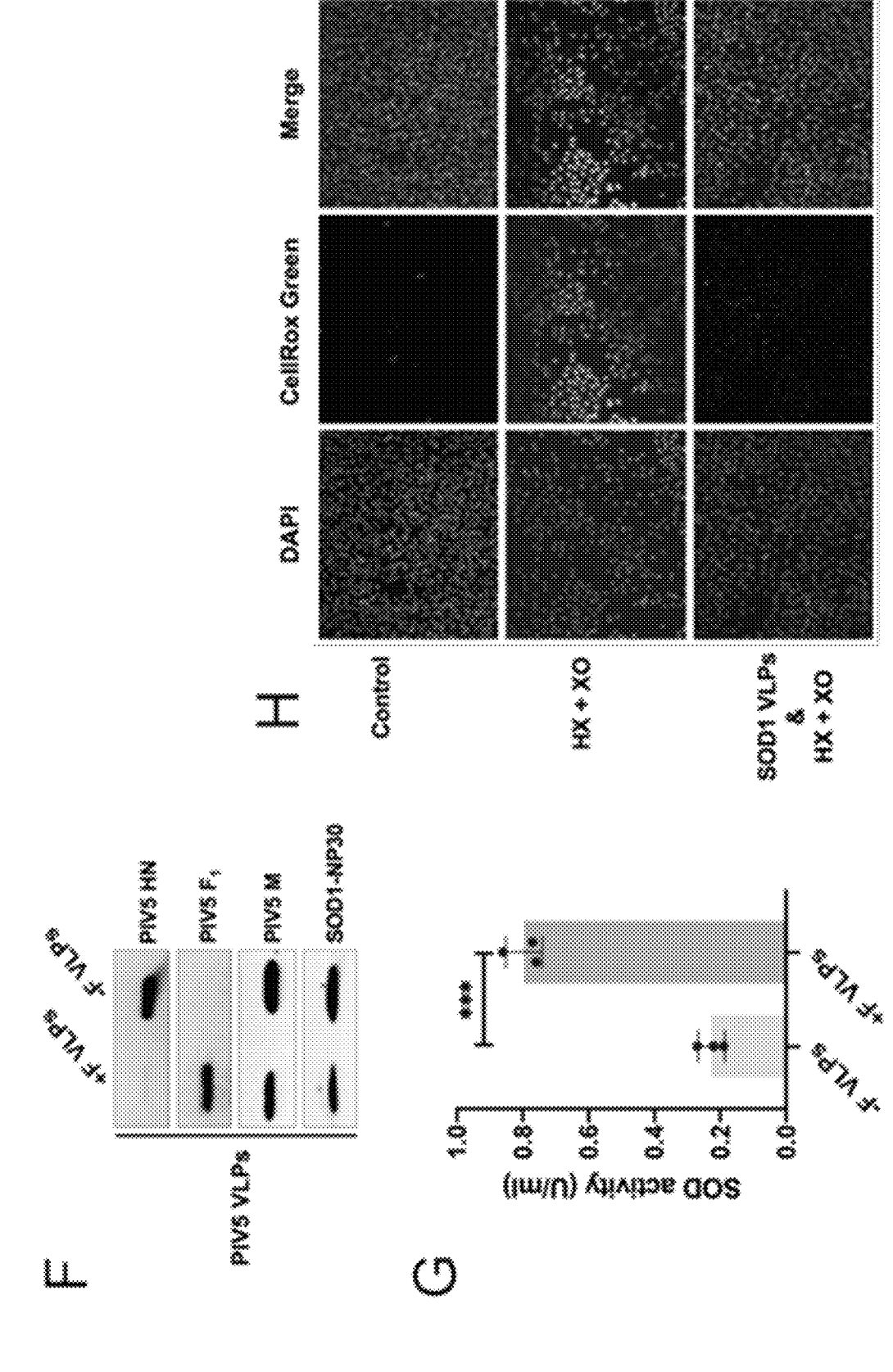

FIG. 5. Delivery of superoxide dismutase to target cells and reversal of oxidative stress. (A) 293T cells were transfected to produce PIV5 M, HN, and F proteins together with modified SOD1 proteins. Cell lysates and sucrose gradient purified VLPs were fractionated on SDS gels, and proteins were detected by immunoblotting. (B) Total amount of SOD1 packaged into VLPs was calculated based on the band intensities observed in panel A, normalized to the value obtained with unmodified SOD1. (C) SOD1 incorporation efficiency was calculated as the amount of SOD1 detected in VLPs divided by the amount of M protein detected in VLPs, normalized to the value obtained with unmodified SOD1. (D) VLP production efficiency was calculated as the amount of M protein detected in VLPs divided by the amount of M detected in cell lysates, normalized to the value obtained with NP protein. (E) Purified VLPs were analyzed as in panel B, but instead of immunoblotting, the amount of SOD1 was measured using an enzymatic assay. (F) Polypeptide compositions of –F and +F SOD1-loaded VLPs, produced as described in Panel A and determined by immunoblotting. (F) SOD1-loaded VLPs were incubated with A549 target cells for 16 h. Residual unfused VLPs were removed by extensive PBS washing. Cells were collected and lysed, and the amount of SOD1 within the cell lysates was measured using an enzymatic activity assay. (H) SOD1-loaded VLPs were incubated with A549 target cells for 16 h. Residual unfused VLPs were removed by extensive PBS washing. Cells were subjected to oxidative stress by incubation with hypoxanthine (150 μM) together with xanthine oxidase (25 mU/ml) for 24 h. Culture medium was replaced with fresh medium containing CellRox Green dye and incubated for 30 min. Cells were then washed with PBS, stained with DAPI, and visualized using a fluorescence microscope. Error bars indicate standard deviations (n=3). *P<0.05, P<0.01, *P<0.001, Welch's t-test.

Figure 6:
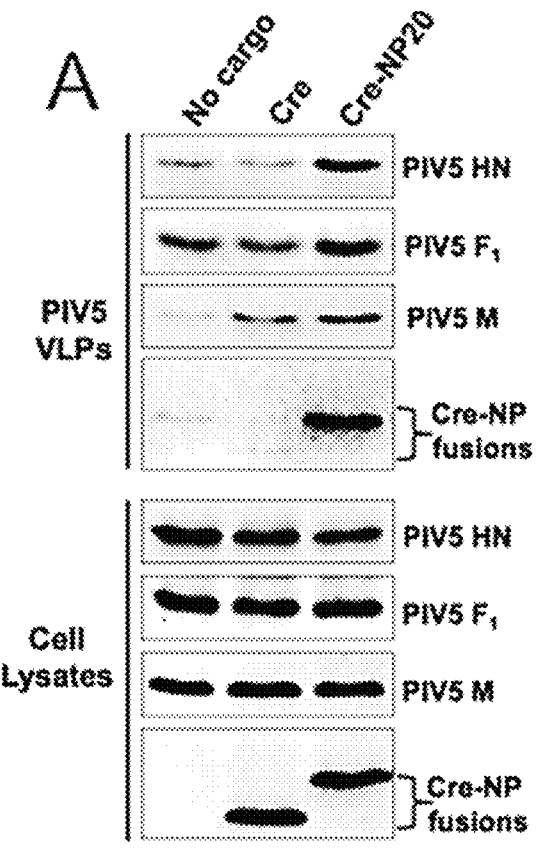
Figure 6:
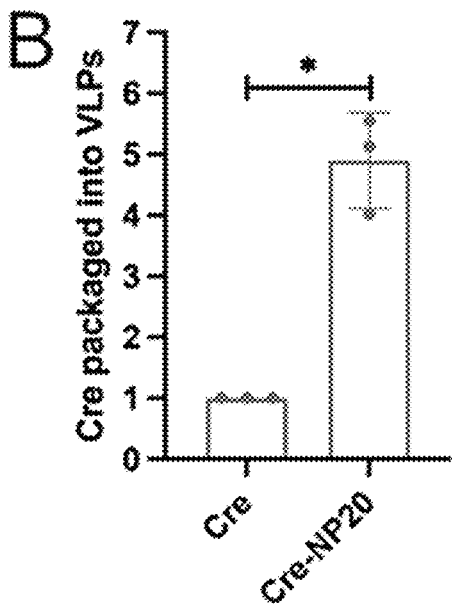
Figure 6:
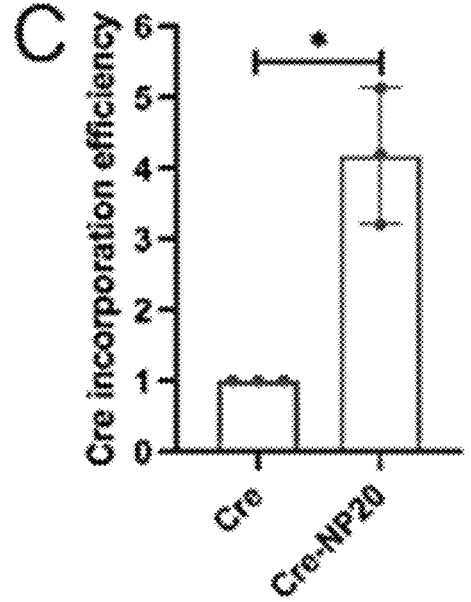
Figure 6:
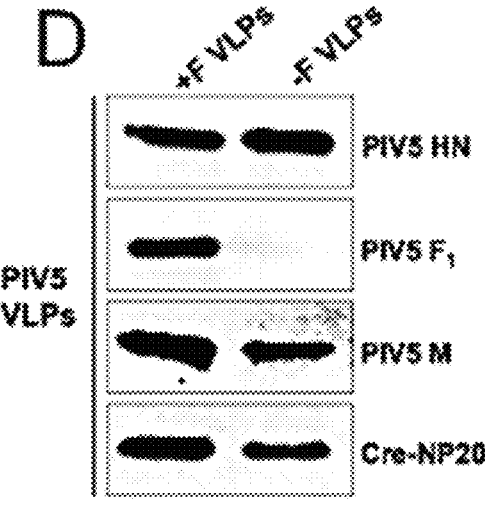
Figure 6:
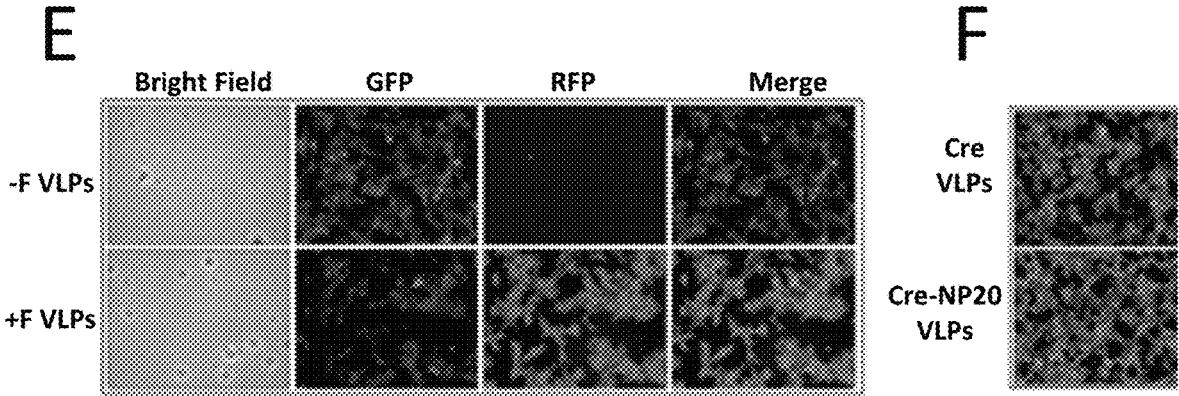
Figure 6:
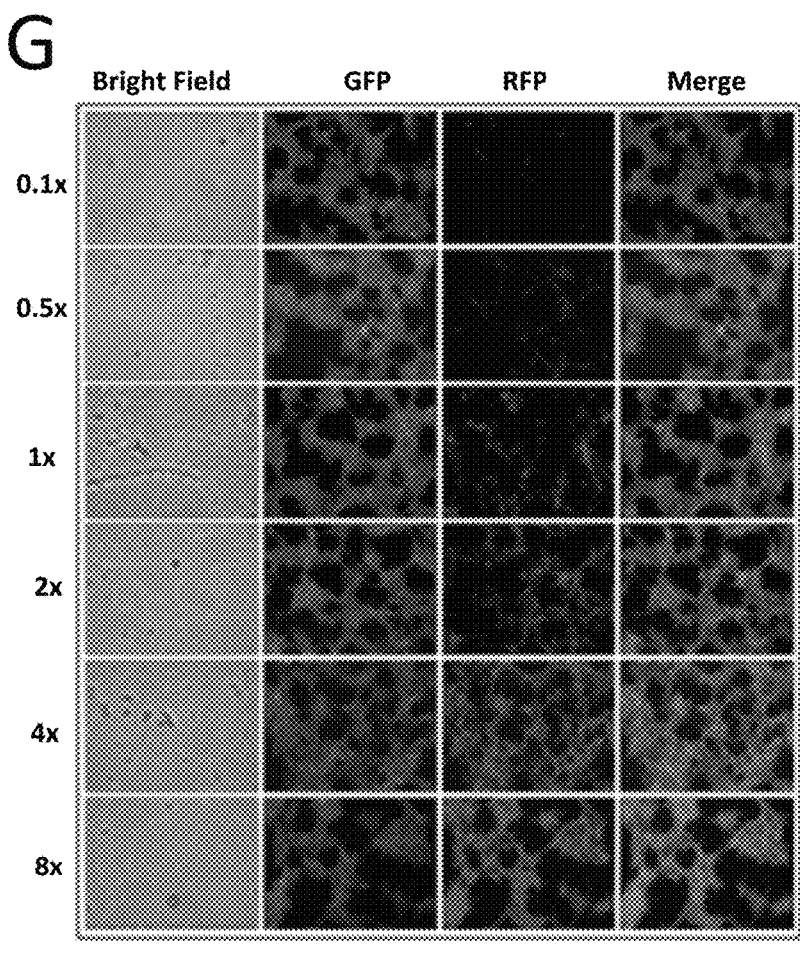
Figure 6:
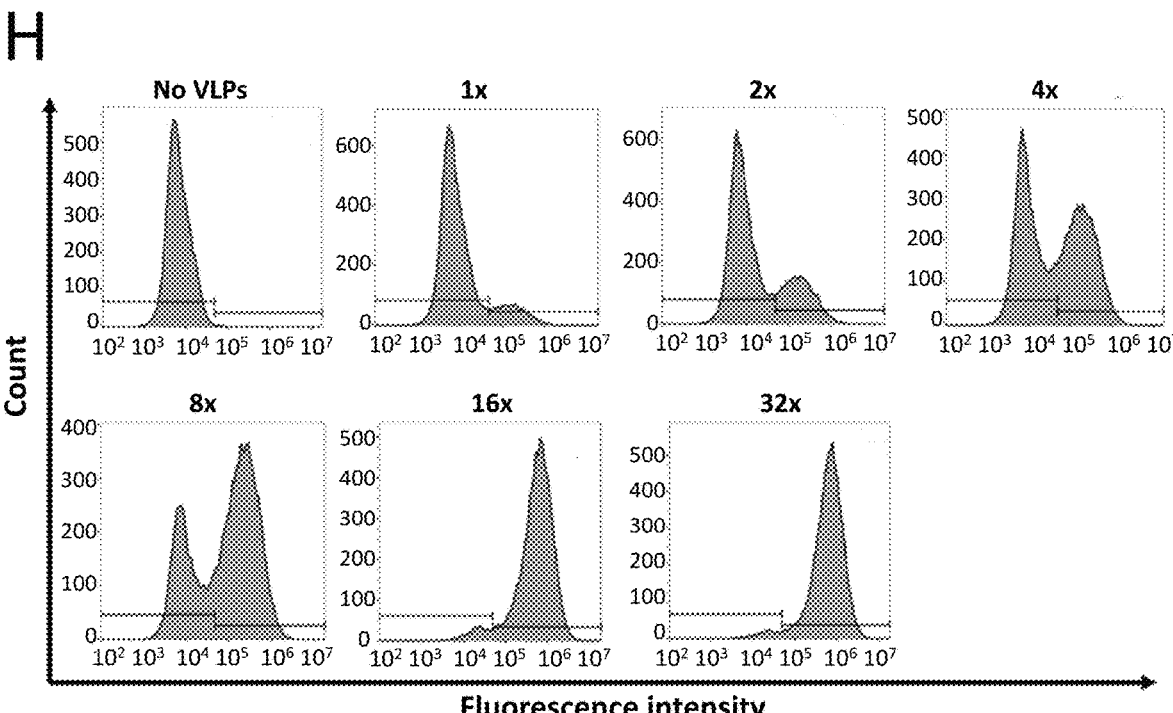
Figure 6:
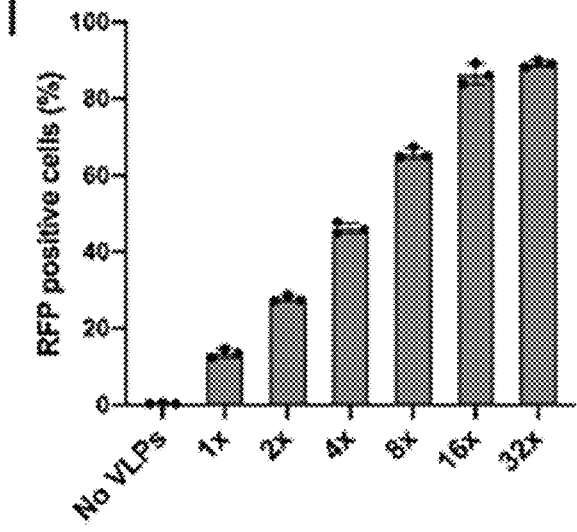

FIG. 6. Delivery of Cre recombinase to target cell nuclei. (A) 293T cells were transfected to produce PIV5 M, HN, and F proteins together with modified Cre proteins. Cell lysates and sucrose gradient purified VLPs were fractionated on SDS gels, and proteins were detected by immunoblotting. (B) Total amount of Cre packaged into VLPs was calculated based on the band intensities observed in panel A, normalized to the value obtained with unmodified Cre. (C) Cre incorporation efficiency was calculated as the amount of Cre detected in VLPs divided by the amount of M protein detected in VLPs, normalized to the value obtained with unmodified Cre. (D) Polypeptide compositions of –F and +F Cre-loaded VLPs, produced as described in Panel A and determined by immunoblotting. (E-I) The indicated doses of Cre-loaded VLPs were incubated for 48 h with 293-loxP-GFP-RFP dual reporter target cells. Cells were washed with PBS, then GFP and RFP fluorescence signals were visualized either using a fluorescence microscope (E, F, G), or using a flow cytometer (H, I). A 1× dose is defined as ¹⁄₄₀ the amount of VLPs harvested from one 10 cm dish of producer 293T cells. For panel E, the dose was set to 20×. Error bars indicate standard deviations (n=3). *P<0.05, Welch's t-test.

Figure 7:
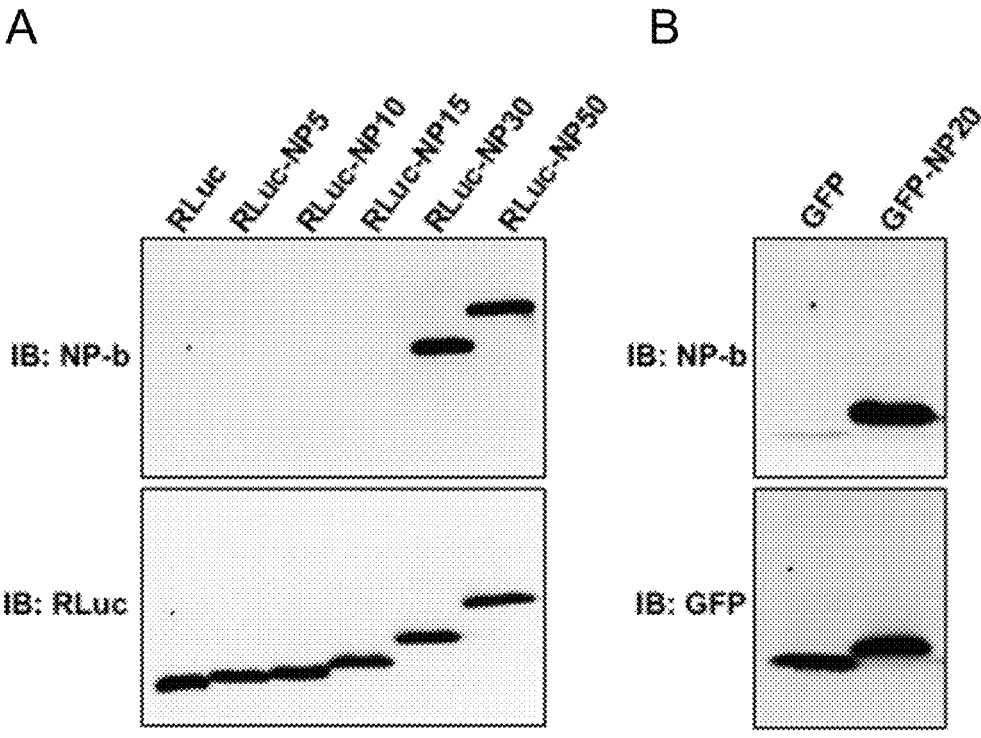

FIG. 7. NP20 functions as an epitope tag in addition to a viral packaging sequence. (A) 293T cells were transfected to express the indicated RLuc or GFP variants. At 24 h post-transfection, cell lysates were prepared and equal portions were fractionated on SDS gels for immunoblot analysis, probing with either anti-RLuc, anti-GFP, or the PIV5 NP-specific monoclonal antibody NP-b, as indicated. (B) Vero cells were transfected to express PIV5 NP or the indicated RLuc and GFP variants. At 24 h post-transfection, cells were fixed, permeabilized, and incubated with NP-b, followed by an Alexa Fluor 594-conjugated secondary antibody. Cell nuclei were stained with DAPI. Cells were visualized using a fluorescence microscope. IB, Immunoblot.

Figure 8:
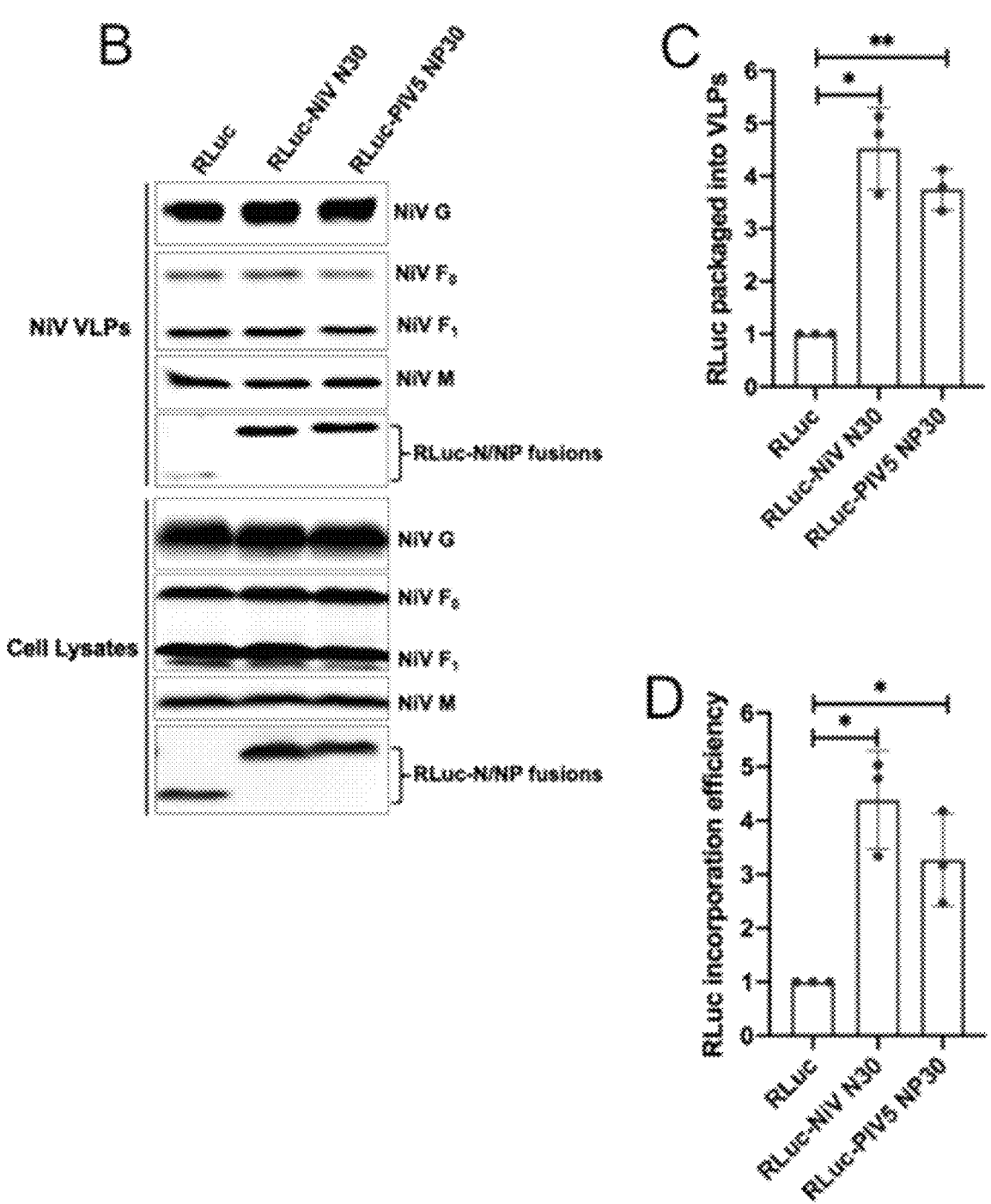
Figure 8:
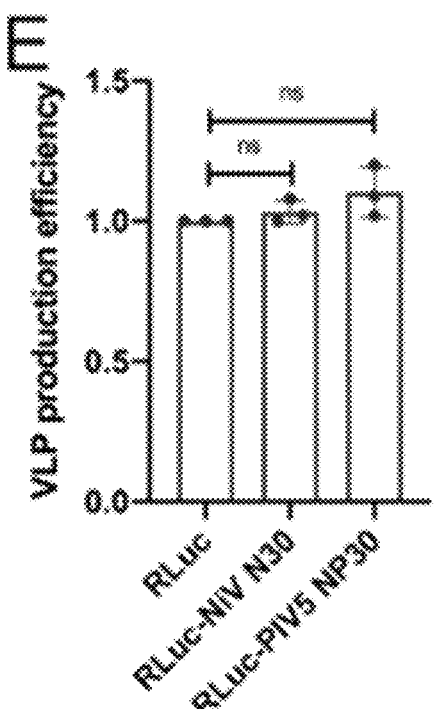
Figure 8:
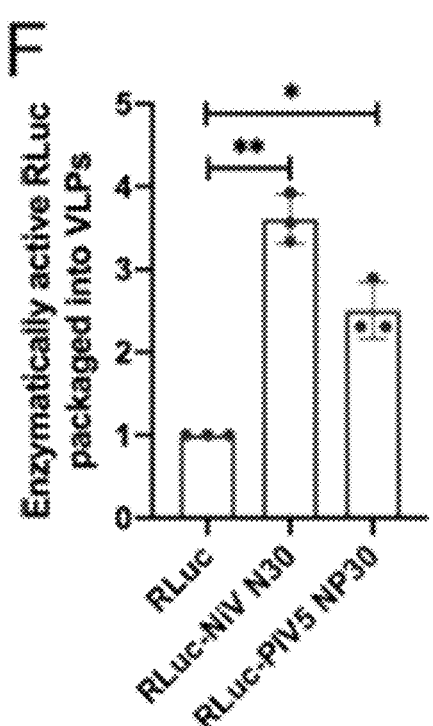
Figure 8:
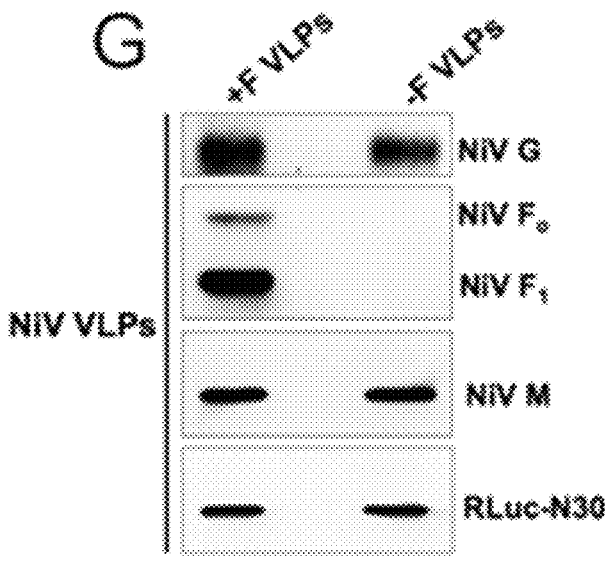
Figure 8:
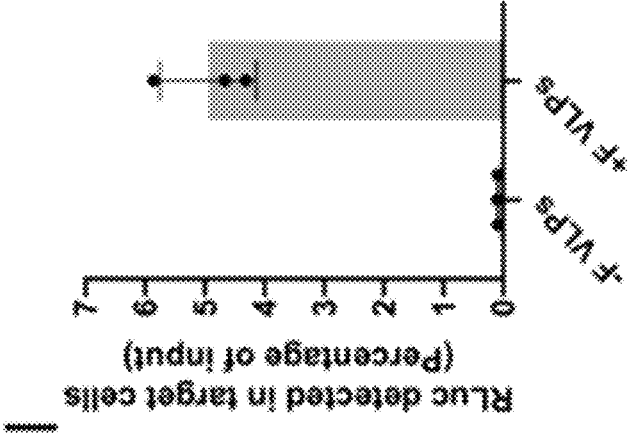
Figure 8:
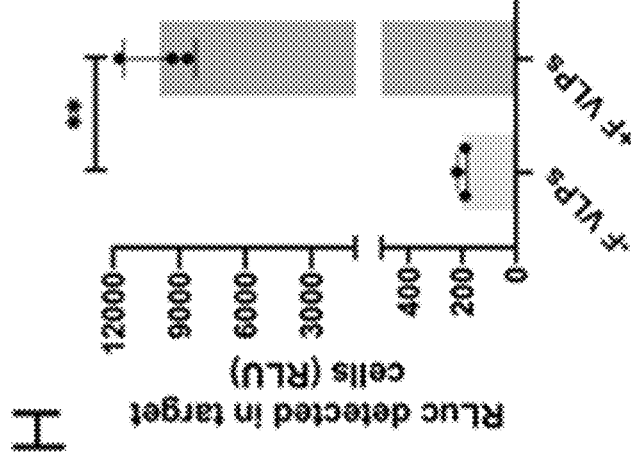

FIG. 8. NiV VLP delivery of Renilla luciferase to target A549 cells. (A) C-terminal amino acid residues of PIV5 and Nipah virus nucleocapsid proteins, with DLD sequences highlighted. The sequence of the PIV5 terminal amino acids is SEQ ID NO:1. The sequence of the Nipha terminal amino acids is SEQ ID NO:4. (B) 293T cells were transfected to produce NiV M, G, and F proteins together with RLuc proteins appended with sequences derived from either the C-terminal end of Nipah virus N or the C-terminal end of PIV5 NP. Cell lysates and sucrose gradient purified VLPs were fractionated on SDS gels and proteins were detected by immunoblotting. (C) Total amount of RLuc packaged into VLPs was calculated based on the band intensities observed in panel B, normalized to the value obtained with unmodified RLuc. (D) RLuc incorporation efficiency was calculated as the amount of RLuc detected in VLPs divided by the amount of M protein detected in VLPs, normalized to the value obtained with unmodified RLuc. (E) VLP production efficiency was calculated as the amount of M protein detected in VLPs divided by the amount of M detected in cell lysates, normalized to the value obtained with unmodified RLuc. (F) Purified VLPs were analyzed as in panel C, but instead of immunoblotting, the amount of enzymatically active RLuc was measured using a luminometer. (G) Polypeptide compositions of –F and +F RLuc-loaded VLPs, produced as described in Panel B and determined by immunoblotting. (H) RLuc-loaded Nipah VLPs were produced and purified as described in panel B, and quantified using a luminometer. VLP aliquots, each containing 100,000 RLU of RLuc, were incubated with target A549 cells for 24 h. Residual cell bound VLPs were removed by extensive PBS washing, cells were lysed, and RLuc that had been successfully delivered was quantified using a luminometer. (I) RLuc delivery efficiency was calculated as the amount of RLuc activity detected in target cell lysates divided by the total amount of RLuc activity detected in the input VLPs. Error bars indicate standard deviations (n=3). *P<0.05, **P<0.01, ns, not significant, Welch's t-test.

DESCRIPTION

Unless defined otherwise herein, all technical and scientific terms used herein have the same meaning as commonly understood by one of ordinary skill in the art to which this disclosure pertains.

The present disclosure relates to modified virus-like particles of paramyxoviruses, compositions comprising them, and methods of using them for delivery of any particular protein of interest to any of a variety of cells. The cells include but are not necessarily limited to mammalian cells. Generally, the disclosure involves introducing into a cell a foreign protein as an engineered component of a paramyxovirus virus like particle (VLP). The compositions, methods and kits accordingly pertain to modified VLPs that contain a contiguous recombinant polypeptide comprising i) all or a segment of a C-terminal domain of a paramyxovirus nucleocapsid protein and ii) a polypeptide sequence of a distinct protein. Paramyxovirus nucleocapsid proteins are referred to as the "N" protein, but it will be recognized that in certain cases the nucleocapsid protein can be what may be referred to in the art for any particular paramyxovirus as the "NP" protein. The N protein can have an amino acid sequence that is the same as a segment of any naturally occurring N protein, or the sequence of the N protein can be modified, such as to provide for enhanced function. The type of paramyxovirus N protein C-terminal sequence that is used or is modified for use in embodiments of this disclosure is not particularly limited. In non-limiting embodiments, the N protein C-terminal sequence that is used and/or modified is from PIV5, hPIV2, Nipah virus, Hendra virus, mumps virus (MuV), measles virus (MeV), Newcastle disease virus (NDV), Sendai virus (SeV), respiratory syncytial virus (RSV), and human metapneumovirus (hMPV). Non-limiting embodiments of the disclosure are provided using PIV5 VLPs, Nipah VLPs, and mumps VLPs. In certain embodiments, C-terminal segment of the N protein that is present in a fusion with a distinct protein is at least 10 amino acids in length, and can be from 0-120 amino acids in length, and the fusion protein may comprise one or more C-terminal segments, and may comprise any suitable linker or linkers. As will be illustrated in the detailed description and examples, in certain embodiments, the C-terminal segment of the N protein can comprise a DLD or DWD amino acid motif. In certain embodiments, the disclosure includes complexes that comprise non-covalent associations of paramyxovirus M protein, and a fusion protein of this disclosure, wherein the fusion protein comprises a foreign protein and a paramyxovirus N protein C-terminal sequence. Such complexes may be present in VLPs of this disclosure. In embodiments, non-covalent associations of cells and modified VLPs are provided. In embodiments, non-covalent associations of VLPs of this disclosure that are formed between the VLPs and sialic acid are provided. In embodiments, non-covalent associations of VLPs of this disclosure with Ephrin B2, Ephrin B3, SLAM and/or Nectin4 receptors are provided. In certain embodiments, complexes comprising antibodies and VLPs of this disclosure are provided. Expression vectors encoding the fusion proteins are provided, as are cells that contain such expression vectors. Methods of making the VLPs are included, as are isolated and/or purified VLP preparations, wherein the VLPs have been separated from cells, including but not necessarily limited to VLP producer cells. It will be recognized that the VLPs can be made by producing any one or any combination of VLP components recombinantly, i.e., by expression from an expression vector. In embodiments, the VLPs are produced using one or more expression vectors in cells, wherein the cells express at least: paramyxovirus M, N or NP, F and Attachment proteins, non-limiting examples or which are described herein.

In certain implementations the disclosure comprises compositions comprising the VLPs, which may be provided as pharmaceutical compositions. In embodiments the disclosure comprises administering the VLPs and/or compositions comprising them to cells, and/or to individuals in need thereof. The administration results in a foreign protein that is present in a fusion protein of the VLPs being introduced to the cell. Methods of screening for anti-viral compounds are provided. These methods generally comprise determining whether one or more test agents can inhibit one or more steps of viral infection and/or reproduction by mixing modified VLPs of this disclosure, cells and test agents and determining whether or not the test agents inhibit any of the one or more steps. Also provided are kits. The kits can comprise an expression vector encoding a segment of a C-terminal domain of a paramyxovirus nucleocapsid protein in proximity to a cloning site configured so that a polynucle-otide encoding a distinct polypeptide can be introduced into the cloning site. This configuration results in the capability of the expression vector to express the segment of the C-terminal domain and the distinct polypeptide in a contiguous fusion protein, which may be incorporated into VLPs. The kits can comprise at least one additional expression vector encoding at least one additional VLP component, wherein the at least one additional component is selected from a viral matrix protein, a viral attachment glycoprotein, and a viral fusion glycoprotein. Or, a single expression vector can be adapted to express more than one of these proteins.

In an embodiment, the disclosure provides a paramyxovirus VLP comprising a contiguous recombinant polypeptide comprising i) from 10-120 amino acids of a C-terminal domain of a paramyxovirus nucleocapsid (N) protein, and ii) a polypeptide sequence of a distinct protein selected from the group consisting of recombinases, transcription factors, restriction enzymes, integrases, topoisomerases, helicases, and combinations thereof. In embodiments, the distinct protein is a recombinase that is a Cre recombinase, a Flp Recombinase, a Dre recombinase, a Vika recombinase, or a Vika recombinase. Methods comprising administering the VLPs to cells such that a recombination event takes place are included. The method may include providing a DNA template for recombination with a DNA substrate within a cell. The sequences of all of the aforementioned recombinases are known in the art. In one embodiment, the Cre recombinase comprises 343 amino acids. In one embodiment, the Cre recombinase comprises the amino acid sequence set forth in GenBank: QEJ80660.1, from which the amino acid sequence is incorporated herein by reference, or a sequence that is at least 90% identical to that sequence across its entire length.

The following examples are intended to illustrate but not limit the scope of the invention.

EXAMPLES

Figure 1:
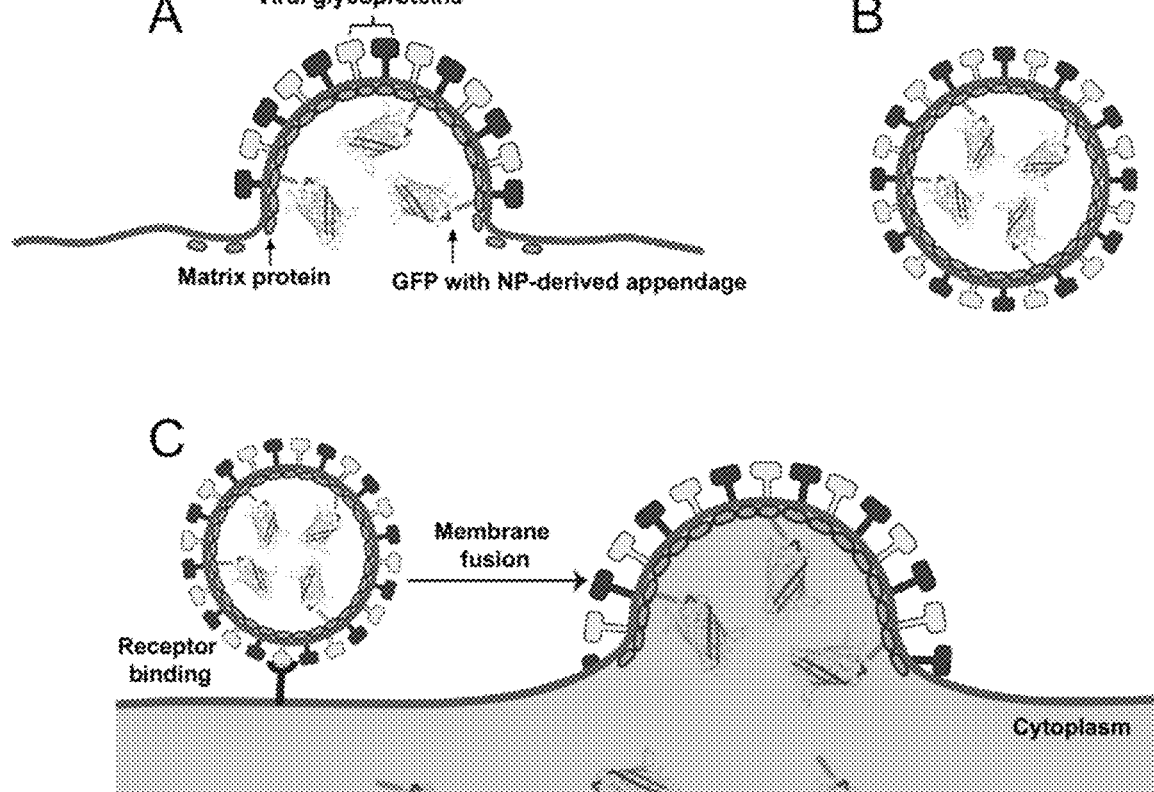
FIG. 1. A strategy for cellular protein delivery using paramyxovirus VLPs. (A, B) Schematic illustration of a GFP cargo, appended with residues derived from a paramyxovirus NP protein, being packaged into budding VLPs using the same interactions that normally direct the packaging of vRNPs into virions. (C) Schematic illustration of a GFP-loaded paramyxovirus VLP after it has bound to a cell surface receptor on a target cell plasma membrane (left) and after the VLP membrane has fused with the target cell plasma membrane, resulting in deposition of GFP into the target cell cytoplasm (right). Cargo proteins are shown enlarged relative to other VLP components for the purpose of illustration, and are not to scale.
Figure 2:
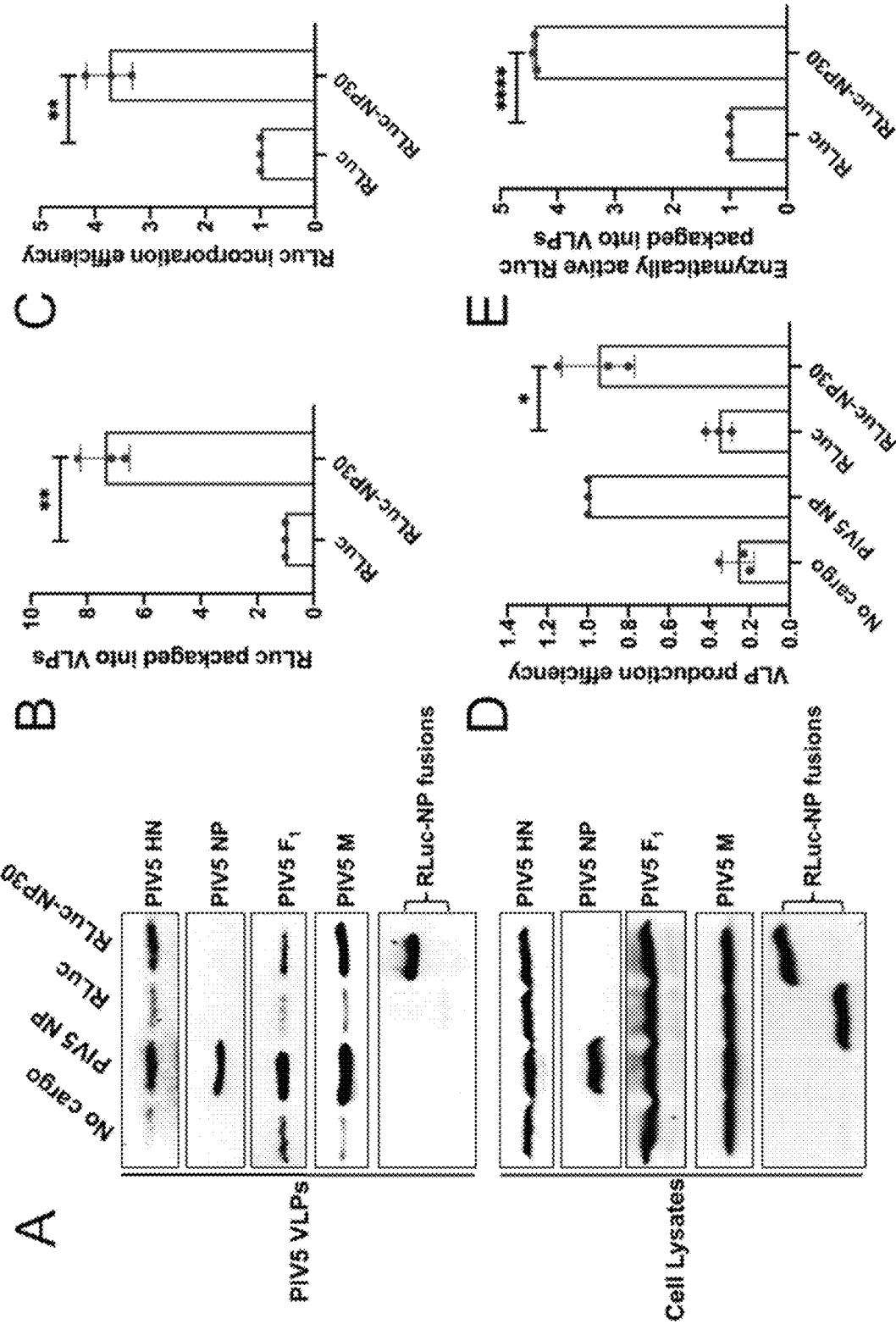
FIG. 2. Production of delivery-capable, luciferase-loaded VLPs. (A) 293T cells were transfected to produce PIV5 M, HN, and F proteins together with either NP-fused RLuc or unmodified RLuc. Cell lysates and sucrose gradient purified VLPs were fractionated on SDS gels, and proteins were detected by immunoblotting. (B) Total amount of RLuc packaged into VLPs was calculated based on band intensities observed in panel A and normalized to the value obtained with unmodified RLuc. (C) Relative efficiency of RLuc incorporation into VLPs was calculated as the amount of RLuc detected in VLPs divided by the amount of M protein detected in VLPs, normalized to the value obtained with unmodified RLuc. (D) Relative levels of efficiency of VLP production were calculated as the amount of M protein detected in VLPs divided by the amount of M detected in cell lysates, normalized to the value obtained with NP protein. (E) RLuc-loaded VLPs were produced and purified as describe for panel A. Purified VLPs were lysed and the amount of enzymatically active luciferase contained within was measured using a luminometer. Readings were normalized to the value obtained with unmodified RLuc. Error bars indicate standard deviations (n=3). *P<0.05, P<0.01, **P<0.0001, Welch's t-test.

Production of delivery-capable, luciferase-loaded VLPs. To evaluate the potential of paramyxovirus VLPs to act as protein delivery vehicles, we first generated VLPs having Renilla luciferase (RLuc) as cargo. The RLuc was appended with a 30 aa residue sequence derived from the C-terminal end of PIV5 NP protein (RLuc-NP30) to direct its packaging into the budding VLPs. A short, flexible GG linker was placed between the RLuc sequence and the NP30 appendage. 293T cells were co-transfected with pCAGGS plasmids encoding the PIV5 matrix protein M, PIV5 surface glycoproteins HN and F, and RLuc-NP30. The resulting VLPs were collected from the culture media, purified using sucrose gradients, and analyzed on western blots (FIG. 2). RLuc-NP30 was efficiently packaged into VLPs, whereas unmodified RLuc was not (FIG. 2A). Moreover RLuc-NP30, similar to authentic PIV5 NP protein, had the ability to stimulate VLP production (judged by the amount of M protein detected in VLP fractions) whereas unmodified RLuc had no such VLP stimulation ability (FIG. 2A). These results are quantified in FIGS. 2 B-D. The total amount of RLuc detected in VLPs was 7-fold higher for RLuc-NP30 as compared to unmodified RLuc (FIG. 2B). Two components contributed for this difference. First, the NP30 appendage enhanced the efficiency of RLuc packaging into the VLPs. RLuc incorporation efficiency (defined as the ratio of RLuc to M in purified VLPs) was 3.7-fold higher for RLuc-NP30 as compared to unmodified RLuc (FIG. 2C). Second, RLuc-NP30 increased the overall efficiency of VLP production by 2.7-fold (defined as the amount of M in purified VLPs divided by the amount of M in the corresponding cell lysates) whereas expression of unmodified RLuc had no significant effects on VLP yield (FIG. 2D). RLuc-NP30 contained within VLPs was enzymatically active, as judged by luminometer readings of purified VLPs shown in FIG. 2E.

Figure 3:
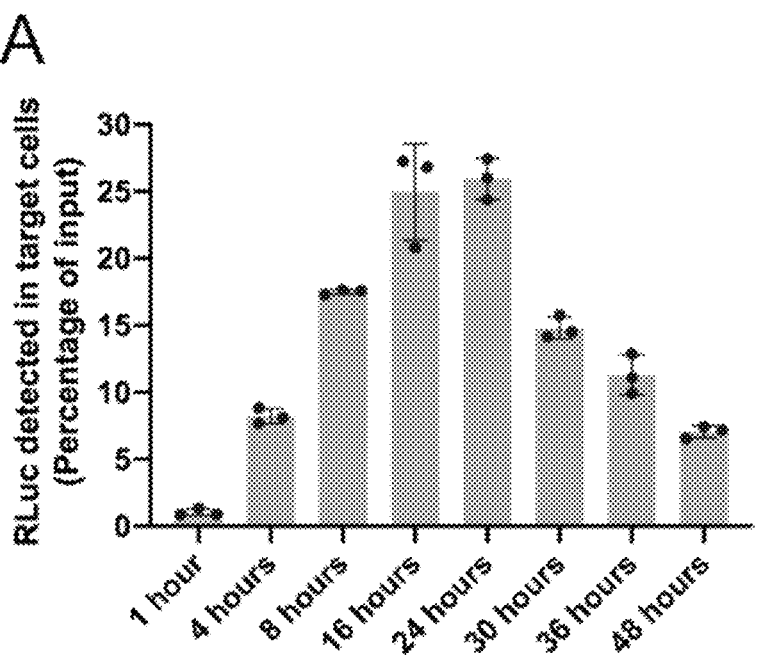
FIG. 3. VLP-mediated delivery of luciferase to target cells. (A) RLuc-loaded PIV5 VLPs were produced and purified as described in FIG. 2, and quantified using a luminometer. VLP aliquots, each containing 100,000 RLU of RLuc-NP30, were incubated with target A549 cells for the indicated lengths of time. Residual cell bound VLPs were removed by extensive PBS washing, cells were lysed, and RLuc that had been successfully delivered was quantified using a luminometer. (B, C) Various quantities of RLuc-loaded VLPs were incubated with A549 target cells as indicated. After 24 h, residual cell-bound VLPs were removed by extensive PBS washing, cells were lysed, and RLuc delivery was quantified using a luminometer. Panel B shows total amounts of RLuc detected in target cell lysates, while panel C shows the amount RLuc detected in target cell lysates as a percentage of the input RLuc. In panels B and C, the bars from left to right in each pairing are −F VLPs and +F VLPs. (D) Polypeptide compositions of −F and +F RLuc-loaded VLPs. VLPs were produced from transfected 293T cells, purified, and analyzed by immunoblotting as in FIG. 2A. Error bars indicate standard deviations (n=3).
Figure 3:
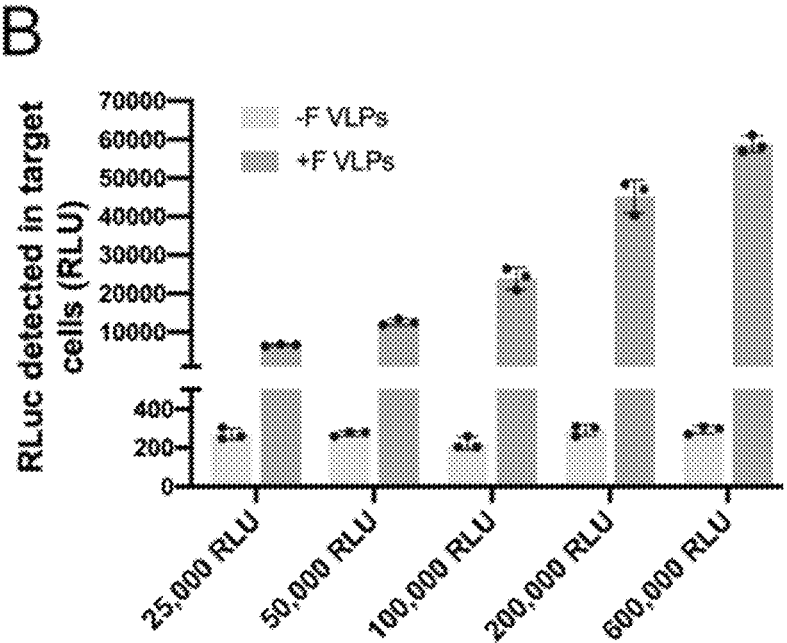
Figure 3:
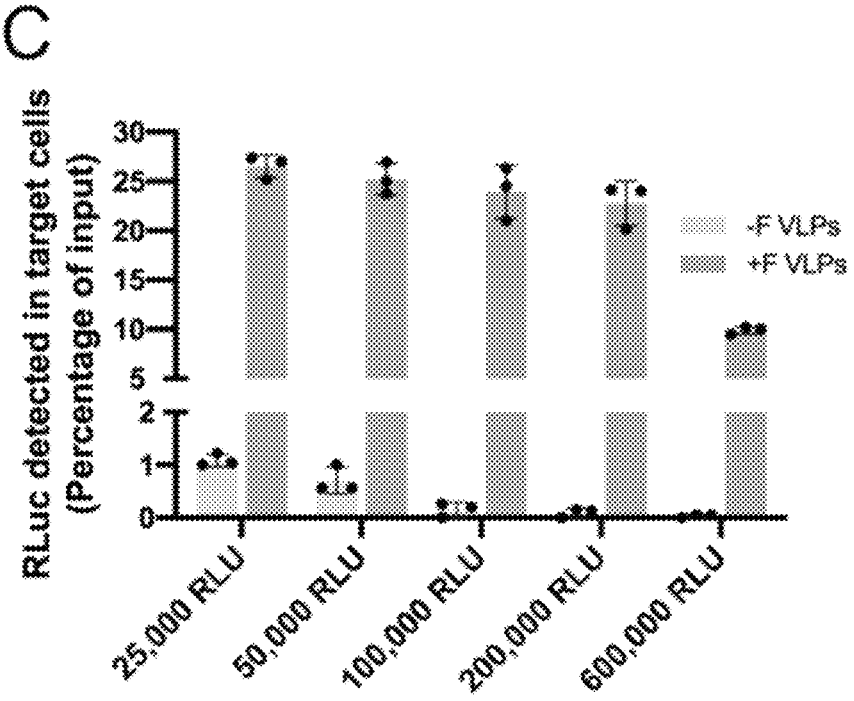
Figure 3:
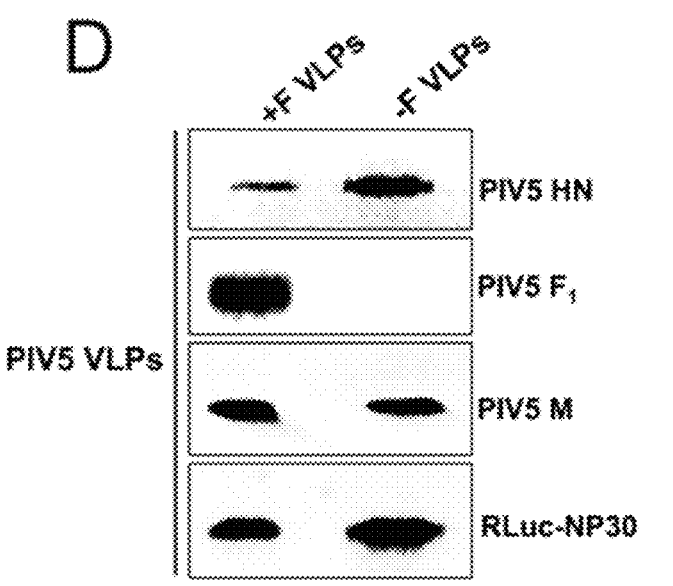

VLP-mediated delivery of luciferase to target cells. Initial delivery experiments were carried out to optimize the length of time that VLPs were incubated with target cells. VLP aliquots, each containing 100,000 RLU of RLuc-NP30, were added to target cells. The VLPs were allowed to incubate with the cells for different lengths of time ranging from 1 h to 48 h. Cells were then washed extensively, lysed, and analyzed for luciferase activity. Peak delivery efficiency was obtained with incubation periods of 16 h or 24 h. Here, about 25% of the input RLuc was recovered from the target cell lysates (FIG. 3A). Incubation periods that were too short (4 h or less) led to delivery efficiencies that were at least 3-fold reduced compared to the 16 h incubation. Incubation periods that were too long (30 h or more) also led to reduced delivery efficiencies, likely due to limited stability of the luciferase cargo after entry into target cells.

Additional delivery attempts were carried out that varied the dose of VLPs added to target cells. VLP aliquots, ranging from 25,000 RLU to 600,000 RLU of RLuc-NP30 activity, were added to target cells and incubated for 24 h. Cells were then washed, lysed, and analyzed for luciferase activity. When doses were in the 25 k-200 k RLU range, increases in VLP dose led to nearly corresponding increases in RLuc delivery (FIG. 3B) and delivery efficiencies were all close to 25% (FIG. 3C). The 600 k RLU dose, however, led to a level of RLuc delivery that was only about 1.3-fold higher than that achieved with the 200 k RLU dose (FIG. 3B), translating to a delivery efficiency of just under 10% (FIG. 3C).

One potential concern with these delivery experiments is the possibility that some VLPs could attach to target cells and remain bound even after extensive washing steps. In this case, luciferase activity readings from cell lysates would be derived not only from RLuc-NP30 that has been delivered to the cell interior, but also from RLuc-NP30 that is still enclosed within residual VLPs that remain bound to the target cells at the time of lysis. To control for this possibility, delivery experiments were performed in parallel with two types of RLuc-loaded VLPs: VLPs having only the attachment glycoprotein HN (attachment-capable but entry-defective) and VLPs having both HN and fusion (F) glycoproteins (entry-capable). Overall VLP production and incorporation of RLuc-NP30 was similar between +F and –F VLPs (FIG. 3D). When used for delivery, –F VLPs led to only negligible detection of RLuc activity in cell lysates (FIGS. 3B-C) indicating that the washing steps were effective and that residual, cell-bound but unfused VLPs did not meaningfully impact delivery measurements.

Delivery of GFP to target cells using VLPs. We next tested if paramyxovirus VLPs would be effective as delivery tools for cargos other than luciferase. Here, GFP was selected as a test cargo as this would also allow easy visualization of cargo within target cells post-delivery. GFP was first modified by transplanting 20 aa residues from the C-terminal end of PIV5 NP onto the C-terminal end of GFP. Three different linker sequences separating GFP from the NP20 sequence were tested: a rigid PAPAP linker, a long flexible (GGGGS)$_3$ linker, and a short flexible GG linker (FIG. 4 A-D and data not shown). 293T cells were co-transfected with pCAGGS plasmids encoding the modified GFP cargos together with the PIV5 M, HN, and F proteins.

Figure 4:
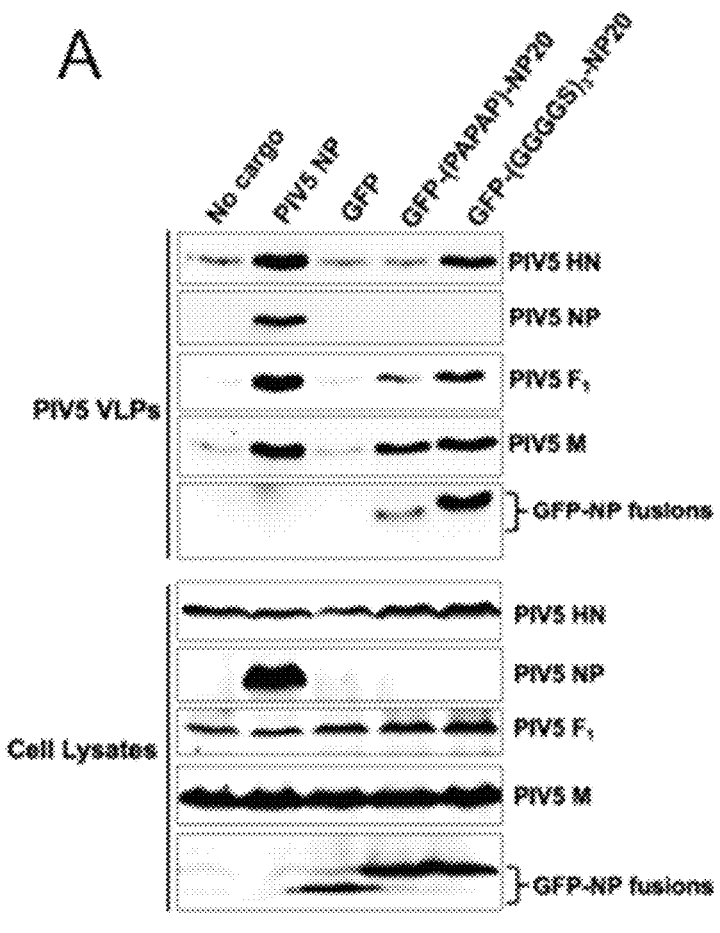
FIG. 4. Delivery of GFP to target cells using VLPs. (A) 293T cells were transfected to produce PIV5 M, HN, and F proteins together with modified GFP proteins. Cell lysates and sucrose gradient purified VLPs were fractionated on SDS gels, and proteins were detected by immunoblotting. (B) Total amount of GFP packaged into VLPs was calculated based on the band intensities observed in panel A, normalized to the value obtained with unmodified GFP. (C) GFP incorporation efficiency was calculated as the amount of GFP detected in VLPs divided by the amount of M protein detected in VLPs, normalized to the value obtained with unmodified GFP. (D) VLP production efficiency was calculated as the amount of M protein detected in VLPs divided by the amount of M detected in cell lysates, normalized to the value obtained with NP protein. (E) Polypeptide compositions of −F and +F GFP-loaded VLPs, produced as described in Panel A and determined by immunoblotting. (F, G) GFP-loaded VLPs were incubated with A549 target cells for 24 h. Residual unfused VLPs were removed by extensive
Figure 4:
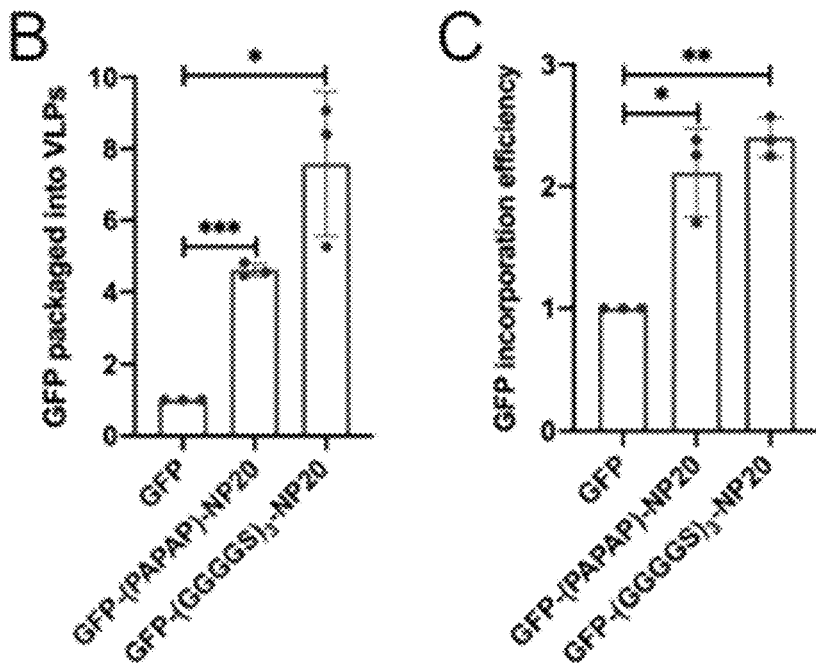
Figure 4:
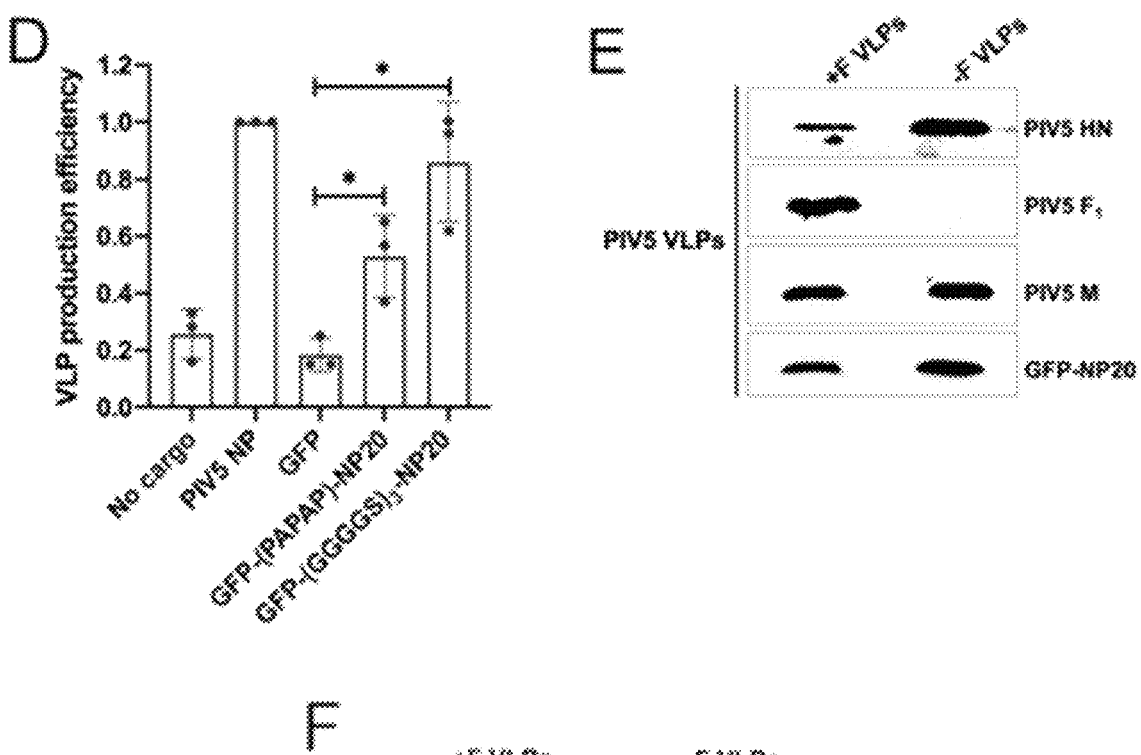
Figure 4:
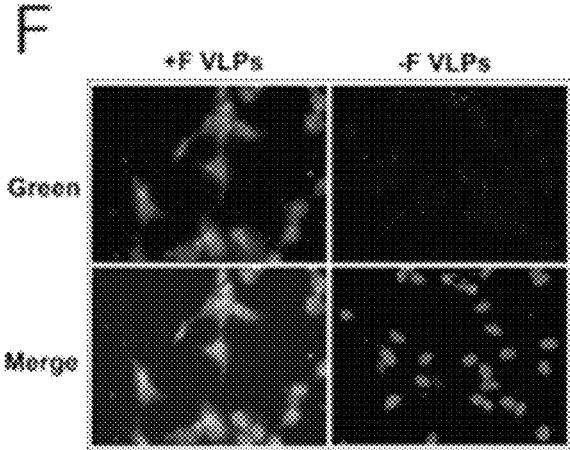
Figure 4:
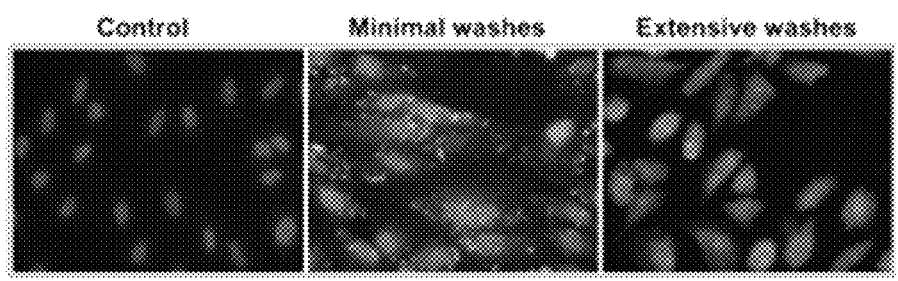

VLPs were collected from the culture media, purified using sucrose gradients, and analyzed on western blots (FIG. 4 A-D). All three linker variants were packaged into VLPs and could stimulate VLP production, whereas unmodified GFP had no appreciable VLP incorporation or ability to stimulate VLP production. The short flexible and rigid linkers led to similar amounts of VLP packaging (data not shown). However, use of the long flexible linker led to VLP packaging that was substantially improved compared to the other two linkers. Hence, subsequent delivery trials were carried out using VLPs loaded with GFP-NP20 harboring the long flexible linker. These VLPs were produced in both the +F and –F configurations. Western blots of purified VLPs confirmed that the GFP-NP20 cargo packaged equally well into +F and –F VLPs (FIG. 4E). The cargo-loaded VLPs were incubated with target A549 cells for 24 h followed by removal of the residual cell-bound VLPs by extensive PBS washing. As shown in FIG. 4F, the delivery of GFP-NP20 to target cell interiors was efficient when cells were incubated with +F VLPs (left panels). However, there was no detectable green fluorescence signal in the cells incubated with –F VLPs (right panels). Additional delivery trials were carried out in which +F VLPs were incubated with A549 target cells followed either by extensive PBS washing (8 washes) or minimal PBS washing (a single wash). After minimal washing, cells were associated with numerous small brightly fluorescent foci, which likely represent intact GFP-loaded VLPs that remain bound to the cell exteriors (FIG. 4G, middle panel). In addition to the foci, a more diffuse green fluorescence signal can also be observed throughout the cells, and this is likely the result of GFP that has been successfully transferred from the VLPs to the cell interiors. For cells that underwent the extensive washing procedure, the brightly fluorescent foci were nearly absent, while the diffuse fluorescence signal throughout the cells remained (FIG. 4G, right panel). Together, these results provide evidence for efficient delivery of protein cargos from paramyxovirus VLPs directly to target cell interiors.

Delivery of superoxide dismutase to target cells and reversal of oxidative stress. Additional packaging and delivery trials were performed with the antioxidant enzyme human SOD1 (superoxide dismutase 1). 30 aa residues from the C-terminal end of PIV5 NP were appended onto the C-terminal end of SOD1 with a short diglycine linker separating SOD1 from the appendage, generating SOD1-NP30. The modified SOD1 was expressed in 293T producer cells together with PIV5 M, HN, and F proteins. VLPs were collected from the culture media, purified by centrifugation through sucrose cushions, and analyzed on western blots (FIG. 5 A-D). Enzymatically active SOD1-NP30 was packaged into VLPs and could stimulate VLP production, while unmodified SOD1 had no such abilities (FIG. 5 A-E). +F and –F versions of the SOD1-loaded VLPs were prepared for delivery trials (FIG. 5F). The VLPs were incubated with target A549 cells for 16 h, then the cells were washed extensively and lysed. Cell lysates were then subjected to SOD1 enzymatic activity assays (FIG. 5G). VLP delivery led to SOD1 activity levels that were nearly 4-fold higher than those found in cells treated with control (–F) VLPs (FIG. 6G). To test if this difference in SOD1 levels has a meaningful impact on the ability of cells to cope with an oxidative stress insult, cells were incubated with SOD1-loaded VLPs as before, washed, then subjected to oxidative stress by incubating with hypoxanthine together with xanthine oxidase for 24 h. CellRox Green reagent was then used to detect the presence of reactive oxygen species (ROS) by fluorescence microscopy. Substantial ROS was detected in control cells treated with hypoxanthine/xanthine oxidase, but not in cells that had the benefit of prior incubation with SOD1-loaded VLPs (FIG. 5H). Hence, the quantity of enzyme delivered by the paramyxovirus VLPs was sufficient to exert a useful biological effect on the target cells.

Delivery of Cre recombinase to target cell nuclei. To test the suitability of paramyxovirus VLPs for delivery of nuclear-localized cargos, we appended the NP20 packaging sequence onto Cre recombinase, with a short diglycine linker separating Cre from the appendage. The modified Cre protein was expressed in 293T producer cells together with PIV5 M, HN, and F proteins for production of VLPs. The VLPs were harvested from the culture media, purified, and analyzed on western blots (FIG. 6 A-C). Cre-NP20 was efficiently packaged into VLPs, while unmodified Cre was not.

To test the ability of VLPs to deliver functional Cre cargo to the nuclei of target cells, reporter cells were used that switch from green fluorescence to red fluorescence upon Cre-induced recombination. +F and −F Cre-loaded VLPs were prepared (FIG. 6D) and incubated with the reporter cells for 48 h. Reporter cells were then visualized using a fluorescence microscope (FIG. 6E). A clear switch to red fluorescence was observed in the majority of reporter cells incubated with +F VLPs, but no switch was observed for cells incubated with the control −F VLPs (FIG. 6E). The extent of Cre recombination and conversion from green to red fluorescence was directly impacted by the VLP dose (FIG. 6 F-H). At the highest doses of VLPs, close to 90% of the cells had converted to red fluorescence (FIG. 6 G-H). This result shows the applicability of using paramyxovirus VLPs for highly efficient delivery of protein cargos that function in the cell nucleus.

NP20 functions as an epitope tag in addition to a viral packaging sequence. During the course generating data described herein, we noticed in some instances that cargo proteins appended with NP-derived sequences could be detected on western blots that were probed with the monoclonal antibody NP-b (Randall, 1987), which is specific to the PIV5 NP protein. This suggested to us that the epitope recognized by NP-b (which has not previously been mapped) might be localized to the same C-terminal sequence that functions for packaging of NP into virions/ VLPs. To explore this possibility further, we examined a series of RLuc variants appended with sequences derived from the C-terminal end of NP. These sequences correspond to the C-terminal 5, 10, 15, 30, or 50 aa residues of NP protein. In earlier experiments with these same RLuc variants, we found that transplanting as few as 15 residues from PIV5 NP onto RLuc was sufficient to direct the modified RLuc into budding VLPs (31). Here, the RLuc variants were expressed in transfected 293T cells, then detected on immunoblots probed with either a RLuc-specific polyclonal antibody or the NP-b monoclonal antibody (FIG. 7A, left panel). As expected, unmodified RLuc could not be detected using the NP-b antibody. Likewise, RLuc appended with 5, 10, or 15 residues derived from the C-terminal end of PIV5 NP could not be detected by NP-b. However, RLuc-NP30 and RLuc-NP50 were each clearly detected on blots probed with NP-b (FIG. 7A). Furthermore, GFP appended with 20 aa residues derived from the C-terminal end of NP could be detected on immunoblots by NP-b, whereas unmodified GFP could not (FIG. 7A, right panel).

To test if cargo proteins could also be detected under nondenaturing conditions, indirect immunofluorescence microscopy experiments were employed (FIG. 7B). RLuc and GFP variants described above were expressed in Vero cells by transient transfection. The cells were permeabilized, incubated with NP-b followed by a red fluorescent (Alexa Fluor 594) conjugated secondary antibody, then visualized using a fluorescence microscope. All of the cargo variants that were detected by NP-b on immunoblots (i.e., GFP-NP20, RLuc-NP30, and RLuc-NP50) were also detected by NP-b using immunofluorescence microscopy (FIG. 7B). In addition, RLuc-NP15 could be detected by immunofluorescence microscopy, even though it was not detected by immunoblot. RLuc-NP5, RLuc-NP10, unmodified RLuc, and unmodified GFP were not detected by NP-b using either method. Overall, these results indicate that the same NP-derived appendages that confer VLP packaging ability to cargo proteins also function as epitope tags for the NP-b monoclonal antibody.

Delivery of a protein cargo to cells using Nipah VLPs. To test more generally the idea that paramyxovirus VLPs can function as protein delivery vehicles, we generated cargo-loaded VLPs using Nipah virus components. Although Nipah virus and PIV5 are not closely related phylogenetically, the C-terminal domains of their NP/N proteins share DLD residues that are critical for genome packaging (FIG. 8A). This results in a high degree of compatibility between the nucleocapsid and matrix proteins of these two viruses, which allows, for example, the PIV5 NP protein to be packaged into Nipah VLPs. Here, we produced Nipah VLPs by coexpression of the Nipah virus M, F, and G proteins in 293T cells, together with a RLuc cargo. Three versions of the luciferase cargo were used—one appended with the C-terminal 30 aa residues of Nipah virus N, one appended with the C-terminal 30 aa residues of PIV5 NP, and one with no appendage. Both RLuc-NiV N30 and RLuc-PIV5 NP30 were efficiently packaged into VLPs, recapitulating the intercompatibility that was observed previously with full-length viral proteins (FIG. 8 B-D). Unmodified RLuc, on the other hand, incorporated poorly into the Nipah VLPs (FIG. 8 B-D). Unlike the situation with PIV5 VLPs where the presence of a functional cargo enhances overall VLP production (FIG. 2D), Nipah VLP production was not enhanced by the presence of the appended luciferase variants (FIG. 8E). This is because Nipah virus M protein by itself is sufficient for high-level VLP production, irrespective of the presence of a cargo protein (10, 11). Modified luciferase proteins contained within the VLPs were enzymatically active, as judged by luminometer readings of purified VLPs shown in FIG. 8F.

+F and −F versions of the RLuc-NiV N30-loaded VLPs were prepared for delivery trials (FIG. 8G). The VLPs were incubated with target A549 cells for 24 h, then the cells were washed extensively and lysed. Cell lysates were then assayed for the presence of luciferase using a luminometer (FIG. 8H-I). Significant delivery of luciferase to the target cells was observed for the +F Nipah VLPs, with about 5% of the input RLuc detected in target cell lysates, whereas no delivery was observed for the −F control VLPs (FIG. 8 H-I). Hence, different paramyxovirus VLPs having disparate cell surface receptor targets and tropisms can be manipulated to serve as delivery vehicles for protein cargos that have been modified with short C-terminal appendages.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A paramyxovirus virus like particle (VLP) comprising a contiguous recombinant polypeptide comprising i) a segment of a C-terminal domain of a paramyxovirus nucleocapsid (N) protein, and ii) a polypeptide sequence of a distinct protein that is a recombinase, the polypeptide further comprising a nuclear localization signal, and wherein said contiguous recombinant polypeptide exhibits recombinase activity when present in a nucleus.

2. The VLP of claim 1, wherein the segment of the C-terminal domain is from a paramyxovirus that is one of PIV5, hPIV2, Nipah virus, Hendra virus, mumps virus (MuV), measles virus (MeV), Newcastle disease virus (NDV), Sendai virus (SeV), and human metapneumovirus (hMPV).

3. The VLP of claim 2, wherein the recombinase is Cre recombinase.

4. The VLP of claim 1 wherein the VLP is present in a composition.

5. An expression vector encoding the recombinant protein of the VLP of claim 1.

6. A method comprising contacting a cell with a virus like particle (VLP), the VLP comprising a contiguous recombinant polypeptide comprising i) a segment of a C-terminal domain of a paramyxovirus nucleocapsid (N) protein, and ii) the polypeptide sequence of a distinct protein that is a recombinase, the polypeptide further comprising a nuclear localization signal, and wherein said contiguous recombinant polypeptide exhibits recombinase activity when present in a nucleus.

7. The method of claim 6, wherein the recombinase participates in recombination of a DNA substrate in the cell.

8. The method of claim 7, wherein the recombinase is Cre recombinase.

* * * * *

SEQUENCE LISTING

<160> NUMBER OF SEQ ID NOS: 14

<210> SEQ ID NO 1
<211> LENGTH: 23
<212> TYPE: PRT
<213> ORGANISM: PIV5 virus

<400> SEQUENCE: 1

Gln Asn Ala Ala Val Gly Ala Pro Ile His Thr Asp Asp Leu Asn Ala
1               5                   10                  15

Ala Leu Gly Asp Leu Asp Ile
            20

<210> SEQ ID NO 2
<211> LENGTH: 23
<212> TYPE: PRT
<213> ORGANISM: Mumps virus

<400> SEQUENCE: 2

Glu His Gly Asn Thr Phe Pro Asn Asn Pro Asn Gln Asn Ala Gln Ser
1               5                   10                  15

Gln Val Gly Asp Trp Asp Glu
            20

<210> SEQ ID NO 3
<211> LENGTH: 23
<212> TYPE: PRT
<213> ORGANISM: hPIV2 virus

<400> SEQUENCE: 3

Asp Asp Asp Ala Asn Asp Ala Thr Asp Gly Asn Asp Ile Ser Leu Glu
1               5                   10                  15

Leu Val Gly Asp Phe Asp Ser
            20

<210> SEQ ID NO 4
<211> LENGTH: 23
<212> TYPE: PRT
<213> ORGANISM: NiV virus

<400> SEQUENCE: 4

Ser Glu Lys Lys Asn Asn Gln Asp Leu Lys Pro Ala Gln Asn Asp Leu
1               5                   10                  15

Asp Phe Val Arg Ala Asp Val
            20

<210> SEQ ID NO 5
<211> LENGTH: 23
<212> TYPE: PRT
<213> ORGANISM: NDV virus

<400> SEQUENCE: 5

Gly Thr Pro Gln Ser Gly Pro Pro Thr Pro Gly Pro Ser Gln Asp
1               5                   10                  15

Asn Asp Thr Asp Trp Gly Tyr
            20

<210> SEQ ID NO 6
<211> LENGTH: 23
<212> TYPE: PRT
<213> ORGANISM: SeV virus

<400> SEQUENCE: 6

-continued

---

Gly Arg Asn Asn Gly Val Asp His Asp Glu Asp Asp Thr Ala Ala
1               5                   10                  15

Val Ala Gly Val Gly Gly Ile
            20

<210> SEQ ID NO 7
<211> LENGTH: 23
<212> TYPE: PRT
<213> ORGANISM: MeV virus

<400> SEQUENCE: 7

Gly Ile Leu Glu Glu Gln Gly Ser Asp Thr Asp Thr Pro Arg Val Tyr
1               5                   10                  15

Asn Asp Arg Asp Leu Leu Asp
            20

<210> SEQ ID NO 8
<211> LENGTH: 23
<212> TYPE: PRT
<213> ORGANISM: HRSV virus

<400> SEQUENCE: 8

Asp Leu Thr Ala Glu Glu Leu Glu Ala Ile Lys His Gln Leu Asn Pro
1               5                   10                  15

Lys Asp Asn Asp Val Glu Leu
            20

<210> SEQ ID NO 9
<211> LENGTH: 15
<212> TYPE: PRT
<213> ORGANISM: PIV5 virus

<400> SEQUENCE: 9

Ile His Thr Asp Asp Leu Asn Ala Ala Leu Gly Asp Leu Asp Ile
1               5                   10                  15

<210> SEQ ID NO 10
<211> LENGTH: 15
<212> TYPE: PRT
<213> ORGANISM: artificial sequence
<220> FEATURE:
<223> OTHER INFORMATION: modified viral N protein C terminus

<400> SEQUENCE: 10

Ile His Thr Asp Asp Leu Asn Ala Ala Leu Gly Asp Trp Asp Ile
1               5                   10                  15

<210> SEQ ID NO 11
<211> LENGTH: 12
<212> TYPE: PRT
<213> ORGANISM: artificial sequence
<220> FEATURE:
<223> OTHER INFORMATION: c-myc tag

<400> SEQUENCE: 11

Asn Glu Gln Lys Leu Ile Ser Glu Glu Asp Leu Cys
1               5                   10

<210> SEQ ID NO 12
<211> LENGTH: 6
<212> TYPE: PRT
<213> ORGANISM: Nipha virus

<400> SEQUENCE: 12

```
Asn Asp Leu Asp Phe Val
1               5

<210> SEQ ID NO 13
<211> LENGTH: 6
<212> TYPE: PRT
<213> ORGANISM: Measels virus

<400> SEQUENCE: 13

Asp Arg Asp Leu Leu Asp
1               5

<210> SEQ ID NO 14
<211> LENGTH: 15
<212> TYPE: PRT
<213> ORGANISM: artificial sequence
<220> FEATURE:
<223> OTHER INFORMATION: recombinant protein

<400> SEQUENCE: 14

Leu Lys Pro Ala Gln Asn Asp Leu Asp Phe Val Arg Ala Asp Val
1               5                   10                  15
```